United States Patent [19]

Sit et al.

[11] Patent Number: 4,966,582
[45] Date of Patent: Oct. 30, 1990

[54] INJECTION SITE PLATFORM

[76] Inventors: James K. Sit, 120 Barrypoint Rd.;
William C. Miller, 100 Fairbank Rd.,
both of Riverside, Ill. 60546

[21] Appl. No.: 374,661

[22] Filed: Jun. 30, 1989

[51] Int. Cl.⁵ .......................................... A61M 37/00
[52] U.S. Cl. ................................. 604/86; 604/263;
604/280
[58] Field of Search ................ 604/93, 174, 175, 177,
604/187, 192, 197, 263, 264, 280, 284, 83, 86

[56] References Cited

U.S. PATENT DOCUMENTS

| | | |
|---|---|---|
| 2,129,983 | 9/1938 | Bacon . |
| 3,029,059 | 4/1962 | Hamilton et al. . |
| 3,332,418 | 7/1967 | Brody . |
| 3,416,567 | 12/1968 | Von Dardel et al. . |
| 3,944,261 | 3/1976 | Reed et al. ................ 604/83 X |
| 4,000,740 | 1/1977 | Mittleman . |
| 4,048,995 | 9/1977 | Mittleman . |
| 4,121,585 | 10/1978 | Becker, Jr. ................ 604/86 |
| 4,183,357 | 1/1980 | Bentley et al. ............. 604/175 |
| 4,405,316 | 9/1983 | Mittleman ................. 604/86 |
| 4,430,077 | 2/1984 | Mittleman ................. 604/111 |
| 4,569,675 | 2/1986 | Prosl et al. ............... 604/175 |
| 4,611,785 | 9/1986 | Steer . |
| 4,636,200 | 1/1987 | Vaillancourt .............. 604/170 |
| 4,650,473 | 3/1987 | Bartholomew et al. .... 604/174 |
| 4,747,835 | 5/1988 | Sandhaus ................. 604/192 |
| 4,827,921 | 5/1989 | Rugheimer ............... 604/284 |
| 4,840,618 | 6/1989 | Marvel .................... 604/187 |

FOREIGN PATENT DOCUMENTS

| | | | |
|---|---|---|---|
| 295888A | 6/1987 | European Pat. Off. ....... | 604/263 |
| 0362625 | 3/1971 | U.S.S.R. ................... | 604/174 |

Primary Examiner—John D. Yasko
Assistant Examiner—Adam J. Cermak
Attorney, Agent, or Firm—Kinzer, Plyer, Dorn, McEachran & Jambor

[57] ABSTRACT

An injection site platform for use in adding a needle injected medication to a parenteral fluid being provided to a patient includes a base and an outlet port of a size and shape to receive a needle piercable resealable diaphragm. There is a conical wall which connects the outlet with the base, with the smaller diameter portion of the conical wall being integral with the outlet and the larger diameter portion terminating at the base. The conical wall provides a needle guide to the diaphragm positioned in the outlet and access for the application of an antiseptic wipe to the diaphragm. A portion of the platform has an opening for a tube carrying parenteral fluid, whereby the tube may be manually constricted by pressing it against the platform adjacent the opening.

11 Claims, 2 Drawing Sheets

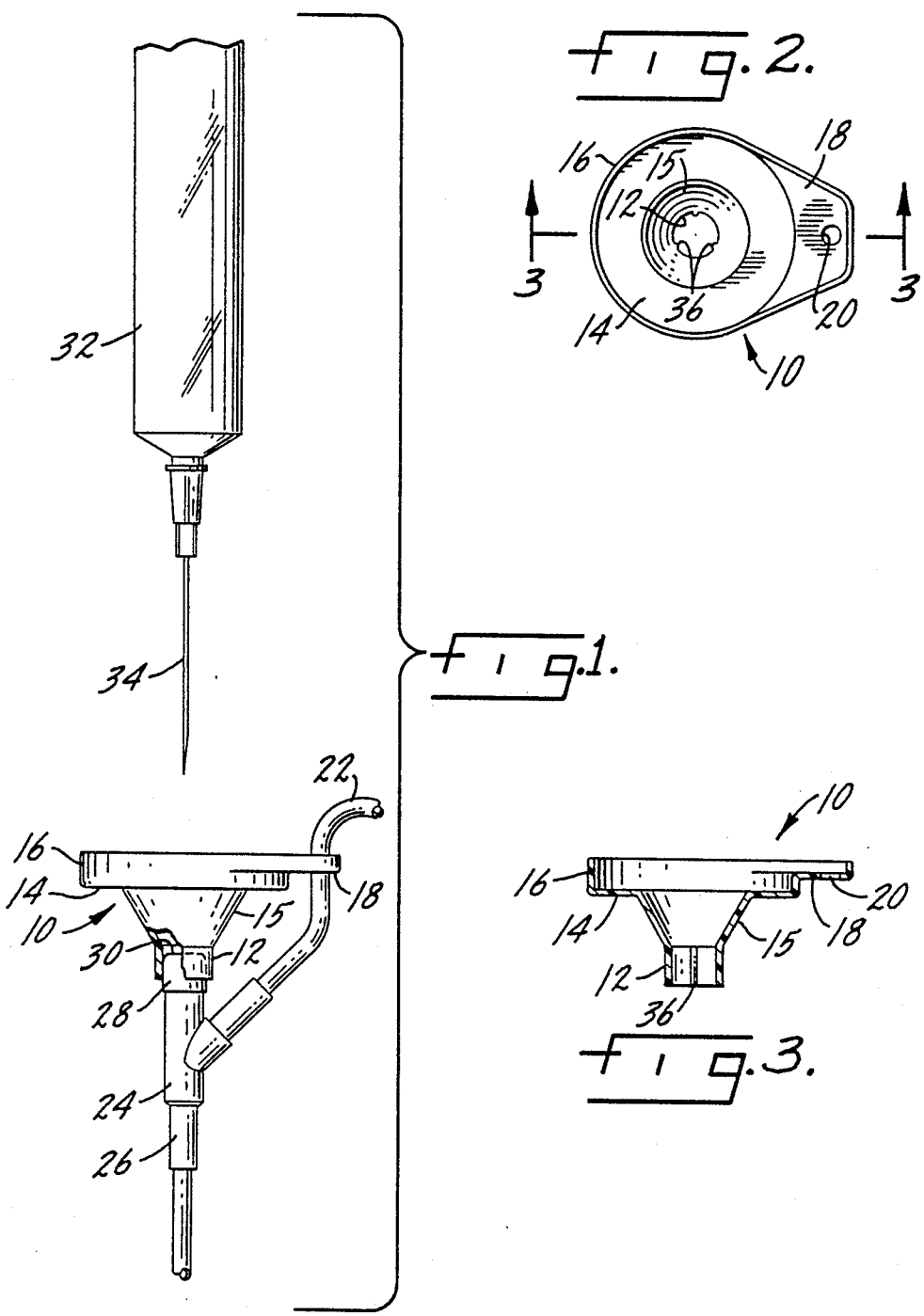

_4,966,582_

INJECTION SITE PLATFORM

SUMMARY OF THE INVENTION

The present invention relates to an injection site platform for use in adding a needle injected medication to a parenteral fluid being provided to a patient and is particularly concerned with a simply constructed platform which insures accurate access to the needle piercable resealable diaphragm and a reliable mean for antiseptically wiping the diaphragm prior to needle insertion.

One purpose of the invention is to provide an injection site platform as described which includes means for constricting the tube carrying parenteral fluid to the patient.

Another purpose of the invention is to provide an injection site platform which has a conical wall which functions as a guide to direct a needle to the needle piercable resealable diaphragm and an access for use in applying an antiseptic wipe to the surface of the diaphragm prior to injection.

Another purpose of the invention is to provide an injection site platform as described in which the platform has a socket for use in removing and reapplying the covering sheath of a hypodermic needle.

Another purpose of the invention is to provide an injection site platform which can accommodate needle sheaths of different size and exterior configuration.

Another purpose of the invention is to provide an injection site platform as described which can accommodate differing size injection port caps having a piercable resealable diaphragm.

Other purposes will appear in the ensuing specification, drawings and claims.

BRIEF DESCRIPTION OF THE DRAWINGS

The invention is illustrated diagrammatically in the following drawings wherein:

FIG. 1 is a side view of the injection site platform of this invention showing a hypodermic needle positioned for insertion therein, FIG. 2 is a top plan view of the injection site platform of FIG. 1, FIG. 3 is a section along plane 3—3 of FIG. 2.

DESCRIPTION OF THE PREFERRED EMBODIMENT

Figure 4:
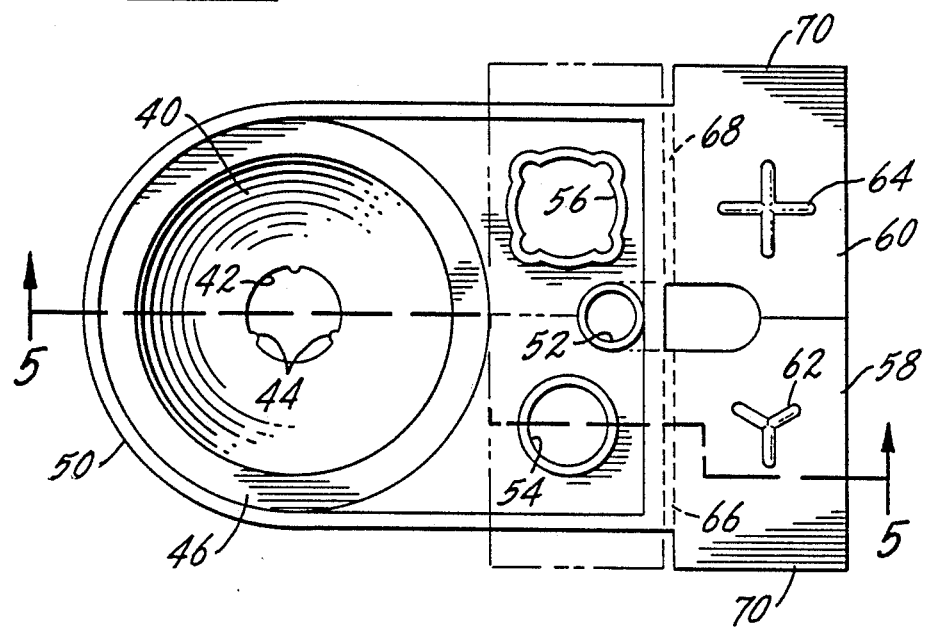
FIG. 4 is a top plan view, similar to FIG. 2, but illustrating a modified form of the invention.

An injection site platform is used to add a needle injected medication to a parenteral fluid which normally is provided intravenously to a patient. The injection site platform of the present invention eliminates the hazard which can result when doctors or nurses inject medication into a intravenous tube in that the invention not only provides a guide for insuring that the needle will be directed toward the resealable diaphragm forming a part of the intravenous fluid apparatus, but also insures that the sheath covering the needle may be removed and replaced without the danger of the needle piercing the hands of the person using it. According to the Centers for Disease Control in Atlanta, the risk of contracting AIDS from being stuck with an AIDS-infected needle is 0.5 percent — one in every 200 instances. Thus, injection site platforms of the type disclosed herein are highly desirable and will become a virtual necessity to reduce the incidence of communicable diseases being transmitted to hospital personnel.

Considering the invention as disclosed in FIGS. 1-3, an injection site platform 10 has a cylindrical outlet 12 and a base 14, all integrally formed by a single injection plastic molding operation. A conical wall 15 joins outlet 12 and base 14. A peripheral upstanding wall 16 surrounds base 14 and there may be a shelf 18 which lies in a plane slightly offset from that of the base 14. As particularly shown in FIG. 2, shelf 18 has an opening 20 which receives a tube 22 of the type used to intravenously feed a parenteral fluid to a patient. Tube 22 is attached to a fitting 24 which has an outlet 26 and an injection port cap 28 formed of a piercable resealable material. The top of cap 28, indicated at 30, forms a resealable membrane to receive the hypodermic needle.

As shown in FIG. 1, a hypodermic syringe 32 having a needle 34 is positioned above and in general alignment with the resealable diaphragm 30. In use, the needle will pierce the diaphragm and the medication therein will be injected into fitting 24. At such time it may be desirable to stop or limit the flow of fluid through tube 22 and this may be done by manually pressing the tube 22 against wall 16 of the platform to either totally constrict fluid flowing through the tube or to partially restrict such flow. The shelf also provides an area for grasping the platform during use.

The conical wall 15 functions as a guide to insure that the needle is directed toward the resealable diaphragm. It also provides a means of access for an antiseptic wipe on the exposed surface of the diaphragm prior to being pierced by the needle.

The cylindrical outlet 12 has a plurality, in this case three, inwardly directed projections or nibs 36 which press against the injection port cap 28 to firmly hold the cap within the injection site platform outlet. The nibs 36 enable the injection site platform to receive injection port caps of slightly differing size and configuration, as the caps of different manufacturers have slightly varying exterior dimensions and shapes.

Figure 5:
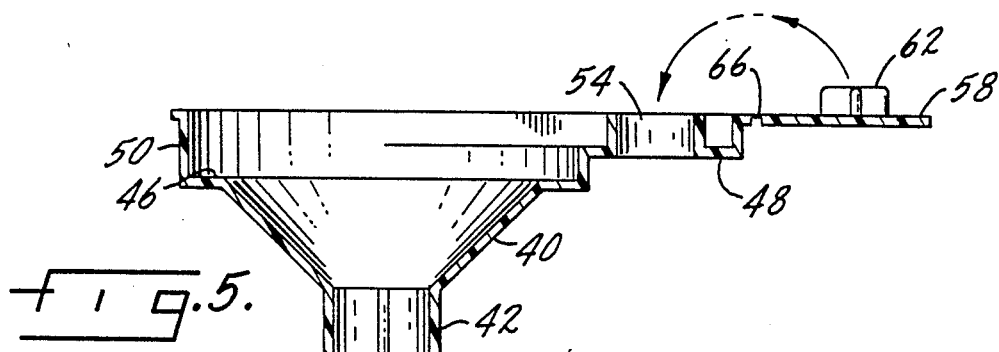
FIG. 5 is a section along plane 5—5 of FIG. 4.

In the invention as disclosed in FIGS. 4 and 5, the injection site platform has a conical wall 40 and an outlet 42 with inwardly directed nibs or projections 44. Conical wall 40 is connected to a base 46 and there is a shelf 48 much as in the FIG. 3-3 embodiment. Base 46 is surrounded by a wall 50 and shelf 48 includes an opening 52 to receive a tube carrying parenteral fluid. Shelf 48 is slightly enlarged over the shelf in the FIG. 1-3 embodiment to provide room for a pair of needle sheath sockets 54 and 56. The sockets differ in size and shape to accommodate the needle sheaths of different manufacturers. There is a cover for each socket, the covers being indicated at 58 and 60, respectively. Each of the covers has differently shaped projections which function to releasably hold each cover in place over its respective socket. Cover 58 has a Y-shaped projection 62 and cover 60 has a cross-shaped projection 64. Each of the covers is hinged, as at 66 and 68, respectively, to the top of platform wall 50. The covers each have a handle 70 which extends beyond wall 50 so that the covers may be moved to an open position for access to the socket.

In the FIG. 4 and 5 embodiment of the invention, the covers 58 and 60 are both hinged along one side of the platform. The FIG. 6 embodiment is the same as in FIGS. 4 and 5, except that both of the covers are hinged to opposite sides of wall 50.

Figure 6:
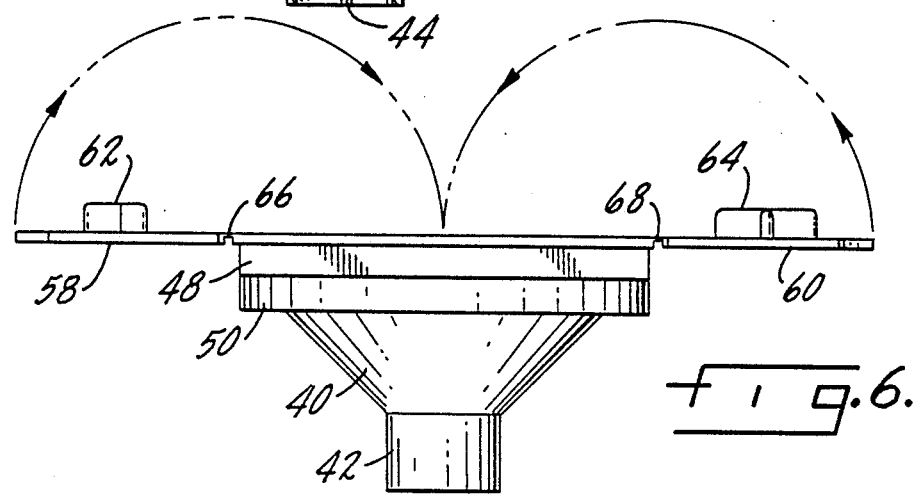
FIG. 6 is a side view of a further alternate embodiment, showing movement of the hinged covers.

In using the invention as shown in FIGS. 4, 5 and 6, medical personnel may use a sheathed needle to first flip open a cover and so expose whichever one of the sockets is appropriate for the particular needle sheath being used. The hypodermic, needle and sheath are pushed into one of the sockets and the hypodermic and needle are removed, leaving the sheath in place within the socket. After the medication has been injected through the resealable diaphragm, the hypodermic and needle may be pushed back into the needle sheath which has remained within the socket. The needle and sheath are then removed from the socket, with the end result that at no time does the hand of the person injecting the medicine have to come at all close to the needle. The sheath is held by the platform as the needle is removed and the sheath is held as it is replaced on the needle. There is almost no likelihood of the needle being near the hands of the person using it.

In other respects the invention shown in FIGS. 4, 5 and 6 functions as shown in FIGS. 1, 2 and 3.

Of particular importance is the fact that the injection site platform can be inexpensively formed of polypropylene or PET in an injection molding machine. The platform provides a fail-safe means for injecting a medication into an intravenous tube. Access to the injection port cap for an antiseptic wipe is provided. There are means for providing fail-safe removal of the needle sheath and for replacing the needle sheath on the needle after use.

Whereas the preferred form of the invention has been shown and described herein, it should be realized that there may be many modifications, substitutions and alterations thereto.

The embodiments of the invention in which an exclusive property or privilege is claimed are defined as follows:

1. An injection site platform for use in adding a needle injected medication to a parenteral fluid being provided to a patient, said platform including a base, an outlet port of a size and shape to receive a needle-pierceable releasable diaphragm, said outlet port having a plurality of inwardly-radially extending projections on the interior thereof so that said outlet port may compressively receive injection port caps having resealable diaphragms of slightly differing size and/or shape, a conical wall with the smaller diameter portion thereof being joined with said outlet and the larger diameter portion thereof being connected to and terminating at said base, whereby said conical wall provides a needle guide to the diaphragm positioned in said outlet and an access for the application of an antiseptic wipe to the diaphragm, a portion of said platform having an opening for use with a tube carrying parenteral fluid, whereby such tube may be manually constricted by pressing the tube against the platform adjacent the opening.

2. The injection site platform of claim 1 further characterized by and including a wall integral with said platform and extending away therefrom, with said opening being adjacent said wall whereby the tube may be manually constricted by pressing the tube against the wall adjacent the opening.

3. The injection site platform of claim 2 further characterized in that said base is planar, said platform includes a shelf, integral with the base, and lying in a plane offset from the plane of said base, said opening being formed in said shelf.

4. The injection site platform of claim 1 further characterized in that said base includes at least one socket having a size and shape to receive the sheath covering a hypodermic needle, whereby a syringe and needle covered by the sheath may be placed in the socket, the socket gripping the sheath to permit removal of the syringe and needle for use in adding a needle injected medication to the parenteral fluid, after which the syringe and needle may be reinserted into the sheath and the sheath removed.

5. The injection site platform of claim 4 further characterized in that there are two sheath sockets on said platform base, said sockets being of different configurations.

6. The injection site platform of claim 5 further characterized in that said sheath sockets are positioned on opposite sides of said opening.

7. The injection site platform of claim 4 further characterized in that said base is planar and includes a peripheral wall extending away therefrom, a shelf forming a part of said platform, and being integral with said base, with said shelf lying in a plane offset from the plane of said base, said opening and said at least one socket being formed in said shelf.

8. The injection site platform of claim 7 further characterized in that there are a pair of sheath sockets on opposite sides of said opening, with said sockets being of different configurations to receive different forms of needle sheaths, and a cover for each socket, said covers being hinged to said peripheral wall.

9. The injection site platform of claim 8 further characterized in that each cover includes means thereon for releasably holding a cover on its respective socket.

10. An injection site platform for use in adding a needle injected medication to a parenteral fluid being provided to a patient, said platform including a base, an outlet port of a size and shape to receive a needle-pierceable resealable diaphragm, a conical wall with the smaller diameter portion thereof being joined with said outlet and the larger diameter portion thereof being connected to and terminating at said base, whereby said conical wall provides a needle guide to the diaphragm positioned in said outlet and an access for the application of an antiseptic wipe to the diaphragm, a portion of said platform having an opening for use with a tube carrying parenteral fluid, whereby such tube may be manually constricted by pressing the tube against the platform adjacent the opening, said base including at least one socket having a size and shape to receive the sheath covering a hypodermic needle, whereby a syringe and needle covered by the sheath may be placed in the socket, the socket gripping the sheath to permit removal of the syringe and needle for use in adding a needle injected medication to the parenteral fluid, after which the syringe and needle may be re-inserted into the sheath and the sheath removed, and a cover for the at least one sheath socket, said cover being attached to said base and being movable to expose the sheath socket.

11. The injection site platform of claim 10 further characterized in that said cover is hinged to said base.

* * * * *